United States Patent
Greyson et al.

(10) Patent No.: US 10,123,961 B2
(45) Date of Patent: Nov. 13, 2018

(54) PERSONAL CARE COMPOSITIONS WITH MODIFIED GUAR DERIVATIVES

(71) Applicants: ROHM AND HAAS COMPANY, Philadelphia, PA (US); DOW GLOBAL TECHNOLOGIES LLC, Midland, MI (US)

(72) Inventors: Andrea V. Greyson, Blue Bell, PA (US); Emmett M. Partain, III, Bound Brook, NJ (US); Thais C. Curcio, Sao Paulo (BR)

(73) Assignees: Rohm & Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/102,582

(22) PCT Filed: Dec. 19, 2014

(86) PCT No.: PCT/US2014/071447
§ 371 (c)(1),
(2) Date: Jun. 8, 2016

(87) PCT Pub. No.: WO2015/095677
PCT Pub. Date: Jun. 25, 2015

(65) Prior Publication Data
US 2016/0310401 A1    Oct. 27, 2016

Related U.S. Application Data

(60) Provisional application No. 61/919,561, filed on Dec. 20, 2013.

(51) Int. Cl.
| | | |
|---|---|---|
| *A61K 8/73* | (2006.01) | |
| *A61Q 5/02* | (2006.01) | |
| *A61Q 5/12* | (2006.01) | |
| *A61K 8/365* | (2006.01) | |
| *A61K 8/37* | (2006.01) | |
| *A61K 8/44* | (2006.01) | |
| *A61K 8/46* | (2006.01) | |
| *A61K 8/86* | (2006.01) | |
| *A61K 8/89* | (2006.01) | |
| *C08B 37/00* | (2006.01) | |

(52) U.S. Cl.
CPC .............. *A61K 8/737* (2013.01); *A61K 8/365* (2013.01); *A61K 8/37* (2013.01); *A61K 8/442* (2013.01); *A61K 8/463* (2013.01); *A61K 8/86* (2013.01); *A61K 8/89* (2013.01); *A61Q 5/02* (2013.01); *A61Q 5/12* (2013.01); *C08B 37/0096* (2013.01); *A61K 2800/5422* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 4,276,414 A | 6/1981 | Tessler | |
| 4,292,212 A * | 9/1981 | Melby | A61K 8/44 424/70.13 |
| 4,472,297 A | 9/1984 | Bolich, Jr. | |
| 6,200,554 B1 * | 3/2001 | Yeoh | A61K 8/39 424/70.11 |
| 7,772,421 B2 * | 8/2010 | Yang | A61K 8/8152 560/205 |
| 7,777,026 B2 * | 8/2010 | Huttermann | A61K 8/737 536/114 |
| 2001/0022967 A1 | 9/2001 | Brandt | |
| 2005/0171344 A1 | 8/2005 | Rinaldi | |
| 2009/0214608 A1 | 8/2009 | Monin | |
| 2011/0142779 A1 | 6/2011 | Drovetskaya | |

FOREIGN PATENT DOCUMENTS

| | | |
|---|---|---|
| CN | 101048132 A | 10/2007 |
| CN | 101248091 A | 8/2008 |
| CN | 101437487 A | 5/2009 |
| WO | 2006/133845 | 12/2006 |

OTHER PUBLICATIONS

International Search Report and Written Opinion of the International Searching Authority, dated May 13, 2015, International Application No. PCT/US2014/071447.
European Search Report for EP 17 19 9634 dated Jan. 26, 2018, pp. 1-6.
The State Intellectual Property Office of the People's Republic of China Search Report for Chinese Patent Application No. CN201480069452.3 dated Jun. 6, 2018, pp. 1-2.

* cited by examiner

*Primary Examiner* — Brian Gulledge
(74) *Attorney, Agent, or Firm* — McDonnell Boehnen Hulbert & Berghoff LLP

(57) ABSTRACT

The disclosure provides personal care composition comprising guar derivative, wherein the guar derivative is chemically modified on the galactomannan polymer through an ethoxyl, propoxyl, or hydroxypropoxyl linking group with a tertiary cyclic amine compound.

18 Claims, 2 Drawing Sheets

UCARE + Polyox | Morpholinylethyl + Polyox | Cationic Guar + Polyox | Placebo

Morpholinylethyl  Cationic Guar
+ Polyox        + Polyox

PERSONAL CARE COMPOSITIONS WITH MODIFIED GUAR DERIVATIVES

CROSS-REFERENCE TO RELATED APPLICATIONS

This application is a U.S. national phase of International Application No. PCT/US2014/071447, filed Dec. 19, 2014 which claims priority to U.S. Provisional Application No. 61/919,561, filed Dec. 20, 2013, the disclosure of which is hereby incorporated by reference in its entirety.

BACKGROUND OF THE INVENTION

Field of the Invention

The disclosure provides personal care compositions comprising guar derivatives, wherein the guar derivative is chemically modified on the galactomannan polymer through an ethoxyl, propoxyl, or hydroxypropoxyl linking group with a tertiary cyclic amine compound.

Description of Related Art

Conditioning is one of the key recognized consumer benefits for hair care products. The number of consumers who daily work with their hair, color and bleach it, and frequently change styles is growing globally at a fast pace. Combined with the damaging effects of the sun, industrial, and urban environments, this trend promotes consumers' concern and awareness of the condition of their hair and stimulates market needs for new, efficient conditioning products and ingredients.

Conditioning is typically achieved through deposition of conditioning agents on hair from leave-on and rinse-off treatments. While depositing conditioning materials from a leave-on treatment is more straight-forward, deposition in a rinse-off formulation could present a challenge. When a rinse-off treatment—for example shampoo or conditioner—is applied, only a small portion of conditioning benefit agents contained in the formulation adsorb on the hair surface and stay behind after the rinsing is complete. Some cationic materials, such as "monoquats" (cationic surfactants) or cationic polymers can be used to enhance this conditioning benefit as they deposit and stay on hair more easily, partially due to the anionic charge of the hair surface. These materials can also assist in delivery of other beneficial agents contained in a rinse-off formulation, such as silicone, sunscreen, fragrance, etc. But, there is a growing concern worldwide over the potential damage to the environment that quaternized materials such as monoquats and polyquats might cause. Aquatic toxicity of these materials has been reported and was found proportional to the level of quaternary substitution.

SUMMARY OF THE INVENTION

In a broad aspect, the disclosure provides efficient, non-quaternary personal care compositions that deliver performance benefits and improved toxicity profile. Performance benefits may include but are not limited to: sensorial improvement of the wet or dry skin or hair, improved water resistance, reduced buildup, and reduction of combing forces in hair. These personal care compositions comprise one or more of surfactants and a guar derivative. Guar derivatives are prepared by using guar gum as the starting material. Guar gum is a natural, edible polysaccharide obtained by grinding the seeds of the guar plant *Cyamposis tetragonolobus*, and—unlike cellulose—does not require a chemical reaction such as ethoxylation to be rendered water-soluble. As a result, the guar derivatives can have lower cost and higher renewable content (~85%).

Thus, one aspect of the disclosure provides personal care compositions comprising: one or more of surfactants, and a guar derivative, wherein the guar derivative is selected from guar, hydroxypropylguar, hydrophobe-modified guar, hydrophobe-modified hydroxypropyl guar, and carboxymethylguar, each substituted on a galactomannan polymer through an ethoxyl, propoxyl, or hydroxypropoxyl linking group with a group selected from: morpholinyl, imidazolyl, benzimidazolyl, piperazinyl, 4-methylpiperazinyl, 4-ethylpiperazinyl, piperidinyl, and pyrrolidinyl.

In another aspect, the disclosure provides use of these provides personal care compositions is shampoos, conditioning shampoos, rinse-off conditioners, leave-in conditioners, cleansing conditioners, or body washes.

In another aspect, the disclosure provides methods of conditioning hair, the method comprising applying the personal care composition of the disclosure to the hair.

DETAILED DESCRIPTION OF THE INVENTION

Figure 1:
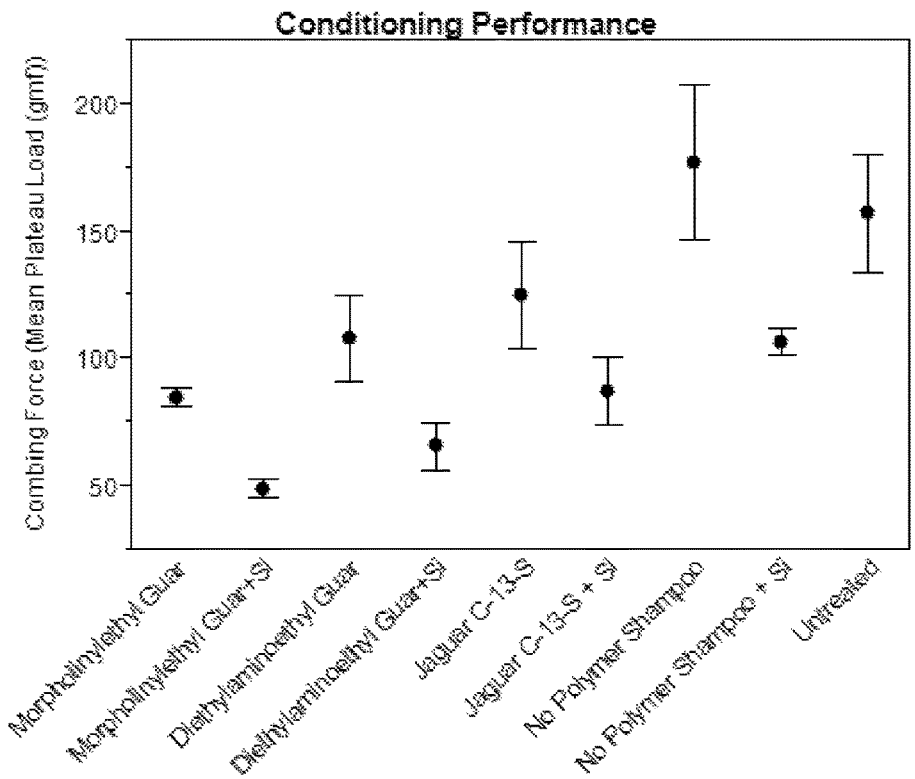
FIG. 1 is a graph depicting the results of an investigation of the performance of a shampoo containing 4-morpholinylethyl guar, a shampoo containing diethylaminoethyl guar, and a shampoo containing cationic guar (JAGUAR™ C-13S, available from Rhodia), in both conditioning and assisted deposition of beneficial agents.

Before the disclosed methods and materials are described, it is to be understood that the aspects described herein are not limited to specific embodiments, or configurations, and as such can, of course, vary. It is also to be understood that the terminology used herein is for the purpose of describing particular aspects only and, unless specifically defined herein, is not intended to be limiting.

In view of the present disclosure, the active materials and methods described herein can be configured by the person of ordinary skill in the art to meet the desired need. In general, the disclosed materials and methods provide improvements in personal care compositions, particularly in hair conditioning compositions. For example, in certain aspect, the personal care compositions of the disclosure (i.e., the compositions that comprise one or more of the guar derivatives) provide performance and reduced aquatic toxicity. Performance benefits may include but are not limited to: sensorial improvement of the wet or dry skin or hair, improved water resistance, reduced buildup, and reduction of combing forces in hair. While not being bound to a particular theory, it is believed that the pKa of the guar derivatives is a key factor to controlling the aquatic toxicity.

In general, "personal care" relates to compositions to be topically applied to a person (including mouth, ear, and nasal cavities, but not ingested). Examples of personal care compositions include skin care products and hair care products. Skin care products include, but are not limited to, facial creams, moisturizers, leave on and rinse off lotions, sunscreens, foundations, mascaras, eye-liners, lipsticks, cleansers, and the like. Hair care products include, but are not limited to, shampoos, leave on and rinse off conditioners, styling gels and hairsprays.

The personal care composition of the disclosure comprise: one or more of surfactants, and a guar derivative, wherein the guar derivative is selected from guar, hydroxypropylguar, hydrophobe-modified guar, hydrophobe-modified hydroxypropyl guar, and carboxymethylguar, each substituted on a galactomannan polymer through an ethoxyl, propoxyl, or hydroxypropoxyl linking group with a group selected from: morpholinyl, imidazolyl, benzimidazolyl, piperazinyl, 4-methylpiperazinyl, 4-ethylpiperazinyl, piperidinyl, and pyrrolidinyl. One skilled in the art will recognize that the ethoxyl ($—O—CH_2CH_2—$), propoxyl ($—O—CH_2CH_2CH_2—$), or hydroxypropoxyl ($—O—CH_2CH(OH)CH_2—$) linking group will depend on the selection of the alkylating agent to make these derivatives (for example, (2-chloroethyl)-, (3-chloropropyl)-, or (2,3-epoxypropyl)-containing alkylating agent), where the oxo moiety (i.e., $—O—$) in the linking group is provided by the galactomannan polymer.

In one embodiment, the substitution on the galactomannan polymer is through an ethoxyl or 2-hydroxypropoxyl linking group. In another embodiment, the substitution on the galactomannan polymer is through an ethoxyl linking group. In another embodiment, the substitution on the galactomannan polymer is through a 2-hydroxypropoxyl linking group. In another embodiment, the substitution on the galactomannan polymer is through a propoxyl linking group.

Other embodiments provide guar, hydroxypropylguar, hydrophobe-modified guar, hydrophobe-modified hydroxypropyl guar, or carboxymethylguar as described above substituted on the galactomannan polymer through the linking group with a group selected from: morpholinyl, imidazolyl, 4-methylpiperazinyl, 4-ethylpiperazinyl, piperidinyl, and pyrrolidinyl. Yet other embodiments provide substitution on the galactomannan polymer through the linking group with morpholinyl, imidazolyl, benzimidazolyl, 4-methylpiperazinyl, or 4-ethylpiperazinyl. Some other embodiments provide substitution on the galactomannan polymer through the linking group with piperidinyl or pyrrolidinyl. Some other embodiments provide substitution on the galactomannan polymer through the linking group with morpholinyl or imidazolyl. In a particular embodiment, guar is substituted through the linking group with morpholinyl or imidazolyl. In another particular embodiment, guar is substituted through the linking group with morpholinyl. In another particular embodiment, guar is substituted through the linking group with imidazolyl.

Exemplary, non-limiting examples of the guar derivatives include 4-morpholinylethyl guar, 3-(1-imidazolyl)-2-hydroxypropyl guar, and 3-(4-morpholinylethyl)-2-hydroxypropyl guar. In one embodiment, the personal care composition is wherein the guar derivative is 4-morpholinylethyl guar. In one embodiment, the personal care composition is wherein the guar derivative is 2-(1-imidazolyl)-2-hydroxypropyl guar. In one embodiment, the personal care composition is wherein the guar derivative is 3-(4-morpholinylethyl)-2-hydroxypropyl guar.

When diluted in an aqueous solution, the guar derivatives as described herein can be evaluated for viscosity. The viscosity can be measured using various types of viscometers and rheometers at about 25.0° C. In certain embodiments, a guar derivative as described herein has a viscosity within the range of from about 500 to about 10,000 mPa-sec at 1% aqueous solution and corrected for ash and volatiles. In other embodiments, the viscosity is about 750 to about 10,000 mPa-sec, or about 1,000 to about 10,000 mPa-sec, or about 1,500 to about 10,000 mPa-sec, or about 2,000 to about 10,000 mPa-sec, or about 3,000 to about 10,000 mPa-sec, or about 500 to about 8,000 mPa-sec, or about 750 to about 8,000 mPa-sec, or about 1,000 to about 8,000 mPa-sec, or about 2,000 to about 8,000 mPa-sec, or about 3,000 to about 8,000 mPa-sec, or about 1,000 to about 5,000 mPa-sec, or about 1,000 to about 4,000 mPa-sec, or about 1,000 to about 3,000 mPa-sec, or about 1,500 to about 5,000 mPa-sec, or about 1,500 to about 4,000 mPa-sec, or about 1,500 to about 3,000 mPa-sec, or about 2,000 to about 5,000 mPa-sec, or about 2,000 to about 4,000 mPa-sec, or about 2,000 to about 3,000 mPa-sec, all at 1% aqueous solution and corrected for ash and volatiles. In one embodiment, the guar derivative as described herein has a viscosity of about 1,000 to about 4,000 mPa-sec at 1% aqueous solution and corrected for ash and volatiles. In another embodiment, the guar derivative as described herein has a viscosity of about 2,000 to about 4,000 mPa-sec at 1% aqueous solution and corrected for ash and volatiles. In another embodiment, the guar derivative as described herein has a viscosity of about 2,000 to about 3,500 mPa-sec at 1% aqueous solution and corrected for ash and volatiles. The person of ordinary skill in the art can, in view of the methods described herein, provide a desired viscosity to guar derivatives.

Similarly, the guar derivatives described herein can be provided with a variety of different molecular weights, depending, e.g., on the methods used for making them and the desired end use. In certain embodiments, a guar derivative as described herein has a molecular weight within the range of from about 50 to about 5,000 kDa. In other embodiments, the molecular weight is about 75 to about 5,000 kDa, or about 100 to about 5,000 kDa, or about 500 to about 5,000 kDa, or about 1,000 to about 5,000 kDa, or about 2,000 to about 5,000 kDa, or about 100 to about 3,000 kDa, or about 500 to about 3,000 kDa, or about 1,000 to about 3,000 kDa, or about 2,000 to about 3,000 kDa, or about 1,000 to about 4,000 kDa, or about 1,500 to about 4,000 kDa, or about 1,500 to about 3,000 kDa, or about 1,000, or about 1,500 kDa, or about 2,500, or about 3,000 kDa, or about 4,000. In one embodiment, the guar derivative as described herein has a molecular weight of about 500 to about 3,000 kDa. In another embodiment, the guar derivative as described herein has a molecular weight of about 1,000 to about 2,000 kDa. The person of ordinary skill in the art can, in view of the methods described herein, provide a desired molecular weight to guar derivatives.

The guar derivatives described herein can have various Kjeldahl nitrogen contents, depending, e.g., on the methods used for making the guar derivative and the desired end use. The Kjeldahl nitrogen content is determined using standard procedures. For example, in certain embodiments, a guar derivative as described herein has Kjeldahl nitrogen content within the range of about 0.02% to about 7.5%. In one embodiment, the Kjeldahl nitrogen content is from about 0.05% to about 7%, or about 0.1% to about 7%, or about 0.5% to about 7%, or about 1% to about 7%, or about 0.05% to about 5%, or about 0.1% to about 5%, or about 0.5% to about 5%, or about 1% to about 5%, about 0.05% to about 3%, or about 0.1% to about 3%, or about 0.5% to about 3%, or about 1% to about 3%, or about 0.1% to about 2.5%, or about 0.5% to about 2.5%, or about 1% to about 2.5%, or about 1.5% to about 2.5%. In one embodiment, the guar derivative as described herein has a Kjeldahl nitrogen content of about 0.1% to about 5%. In another embodiment, the guar derivative as described herein has a Kjeldahl nitrogen content of about 0.2% to about 3%. In another embodiment, the guar derivative as described herein has a Kjeldahl nitrogen content of about 1% to about 2.5%. The person of ordinary skill in the art can, in view of the methods described herein, provide a desired Kjeldahl nitrogen content to guar derivatives.

As the person of ordinary skill in the art will appreciate, the guar derivatives can be provided in various content, depending, e.g., on the desired end properties of the personal care compositions. For example, in certain embodiments, a guar derivative as described herein is present up to 10 weight %, based on the total weight of the personal care composition. In certain embodiments, a guar derivative as described herein is present from about 0.01 weight % to about 10 weight %, based on the total weight of the personal care composition. In other certain embodiments, a guar derivative as described herein is present from about 0.01 weight % to about 2.5 weight %, based on the total weight of the personal care composition. In additional embodiments, a guar derivative as described herein is present from about 0.05 to about 2.5 weight %, or about 0.1 to about 2.5 weight %, or about 0.5 to about 2.5 weight %, or about 1 to about 2.5 weight %, or about 1.5 to about 2.5 weight %, or about 0.01 to about 2 weight %, or about 0.05 to about 2 weight %, or about 0.1 to about 2 weight %, or about 0.5 to about 2 weight %, or about 1 to about 2 weight %, or about 1.5 to about 2 weight %, or about 0.01 to about 1.5 weight %, 0.05 to about 1.5 weight %, or about 0.1 to about 1.5 weight %, or about 0.5 to about 1.5 weight %, or about 1 to about 1.5 weight %, or about 0.01 weight %, or 0.05 weight %, or about 0.1 weight %, or about 0.5 weight %, or about 1 weight %, or about 1.5 weight %, or about 2 weight %, or about 2.5 weight %. In one embodiment, a guar derivative is present from about 0.1 to about 2 weight %, based on the total weight of the personal care composition. One skilled in the art will recognize that the guar derivative may be varied depending on the desired personal care composition. The quantity to be used for the personal care composition of the present disclosure is within the skill of the person skilled in the art using routine trial and experimentation.

The surfactant suitable in the personal compositions of the disclosure may be a cationic, anionic, nonionic, or amphoteric surfactant, or a mixture thereof. One skilled in the art will recognize that the surfactant may be varied depending on the desired composition. The selection of suitable surfactants and the quantity to be used for the personal care formulation of the present disclosure is within the skill of the person skilled in the art using routine trial and experimentation.

In another embodiment, the surfactant is a detergent surfactant. A detergent surfactant is a surface active agent (i.e., a surfactant) that when dissolved in water is able to emulsify oils and hold dirt or other insoluble foreign matter in suspension. This provides the personal care composition with the ability to remove dirt, sweat, sebum, exfoliated skin tissue, and oils from skin and hair. Such surfactants also enable the product to fully wet the skin and hair so that environmental dirt and body secretions can be readily loosened and removed. The detergent surfactants may include any suitable anionic surfactant, non-ionic surfactant, cationic surfactant, amphoteric surfactant, lipoamino acid surfactant, or combinations thereof. Such surfactant may be present in an amount of between about 0 weight % to about 25 weight %, or between about 1 weight % to about 25 weight %, based on the total weight of the personal care composition. In another embodiment, the surfactant may be present in an amount of between about 5 weight % to about 20 weight %, or about 7 weight % to about 18 weight %, or about 5 weight % to about 15 weight %, or about 15 weight % to about 25 weight %, based on the total weight of the personal care composition.

Typical examples of anionic surfactants include soaps, alkylsulfonates, olefinsulfonates, alkylbenzenesulfonates, alkyl ether sulfonates, glycerol ether sulfonates, methyl ester sulfonates, sulfo fatty acids, alkyl sulfates, fatty alcohol ether sulfates, glycerol ether sulfates, fatty acid ether sulfates, hydroxyl mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ethercarboxylic acids and salts thereof, fatty acid isethionates, fatty acid sarcosinates, fatty acid taurides, N-acylaminoacids, such as, for example, acyl lactylates, acyl tartrates, acyl glutamates and acyl aspartates, alkyl oligoglucosidesulfat.es, alkyl glucose carboxylates, protein fatty acid condensates and alkyl (ether)phosphates.

Some examples of cationic surfactants include behentrimonium chloride, alkyltrimethylammonium salts such as cetrimonium bromide and cetrimonium chloride, dimethyldioctadecylammonium chloride, lauryl methyl gluceth-10 hydroxypropyl dimonium chloride, tetramethylammonium hydroxide, dioctadecyldimethylammonium bromide, and the like.

Non-ionic surfactants that may be suitable for use the present disclosure include, but are not limited to, sucrose stearate, sucrose laurate, sucrose palmitate, lauryl glucoside, caprylyl/capryl glucoside, inulin lauryl carbamate, decyl glucoside, polyethylene glycol derivatives of glycerides, ethylene glycol ethers of fatty alcohols, polysorbates, cetyl alcohol, polyoxyethylene glycol alkyl ethers, polyoxypropylene glycol alkyl ethers, glucoside alkyl ethers, and the like.

Lipoamino acid surfactants suitable for use in embodiments of the present invention include sodium cocoyl hydrolyzed wheat protein and sodium cocyl hydrolyzed soy protein (FOAM-SOY C) available from Arch Personal Care Products, South Plainfield, N.J. Lipoamino acid surfactants provide mild cleansing and a rich lather. Other suitable lipoamino acid surfactants include sodium cocoyl glutamate and disodium cocoyl glutamate (PERLASTAN SC 25 NKW or AMISOFT CS-22) available from Schill & Seilacher GmbH (Hamburg, Germany) and Ajinomoto North America (Fort Lee, N.J.), respectively. Another suitable lipoamino acid surfactant is sodium cocoyl alaninate, available under the tradename AMILITE ACS-12 from Ajinomoto North America.

In one embodiment, the surfactant is a nonionic/emulsifier surfactant. In another embodiment, the surfactant is a cationic surfactant, for example behentrimonium chloride. In one embodiment, the cationic surfactant may be present in an amount of between about 0 weight % to about 10 weight %, or between about 0.1 weight % to about 10 weight %, based on the total weight of the personal care composition. In another embodiment, the surfactant may be present in an amount of between about 0.5 weight % to about 7 weight %, or about 1 weight % to about 5 weight %, or about 1 weight % to about 4 weight %, or about 2 weight % to about 4 weight %, based on the total weight of the personal care composition.

In one embodiment, the detergent surfactant is an anionic surfactant optionally in combination with an amphoteric surfactant. In one embodiment, the anionic surfactant is ammonium laureth sulfate, ammonium lauryl sulfate, sodium laureth sulfate, or sodium lauryl sulfate. In one embodiment, the anionic surfactant is present in the amount of between about 1 weight % to about 25 weight %, based on the total weight of the personal care composition. In another embodiment, the anionic surfactant may be present in an amount of between about 5 weight % to about 20 weight %, or about 7 weight % to about 18 weight %, or about 5 weight % to about 15 weight %, or about 15 weight % to about 25 weight %, based on the total weight of the personal care composition.

In one embodiment, the mixture is an anionic surfactant in combination with a second surfactant that is disodium cocoamphodiacetate, decylglucoside, or cocamidopropyl betaine. In one embodiment, the second surfactant is present in an amount from about 1 weight % to about 10 weight %, preferably from about 1 weight % to about 8 weight %, more preferably from about 2 weight % to about 6 weight %, by weight of the personal care composition. In another embodiment, the surfactant is a mixture of sodium laureth sulfate and disodium cocoamphodiacetate. When the surfactant is a mixture of sodium laureth sulfate and disodium cocoamphodiacetate, the ratio of sodium laureth sulfate to disodium cocoamphodiacetate is in a range from about 9:1 to about 1:1, or about 6:1, or about 4:1, or about 2:1.

As the person of ordinary skill in the art will appreciate, the surfactant can be provided in various content, depending, e.g., on the desired end properties of the personal care compositions. The quantity to be used for the personal care composition of the present disclosure is within the skill of the person skilled in the art using routine trial and experimentation.

In one embodiment, the present disclosure provides personal care compositions further comprising a silicone. Silicones include silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxy-diphenylsiloxanes, diphenyl dimethicones, diphenylmethyl-diphenyltrisiloxanes 2-phenylethyltrimethyl siloxysilicates and polymethylphenylsiloxanes, fluoro oils such as partially hydrocarbon-based and/or partially silicone-based fluoro oils, preferably dimethicone, cyclopentasiloxane, cyclohexasiloxane, or a combination thereof. A suitable composition of dimethicone, Laureth-23, and Laureth-4 is commercially available from Dow-Corning via XIAMETER under the trade name XIAMETER MEM-1664 Emulsion, also described as non-ionic emulsion of a -high molecular weight polydimethyl-siloxane. The silicone may be present in a range from about 0.01 weight % to about 5 weight %. In one embodiment, the silicone is present from about 0.5 to about 3 weight %, or about 1 to about 2 weight % of the personal care composition. One of the skill in the art will recognize that the silicone may be varied depending on the desired personal care composition. The quantity to be used for the personal care composition of the present disclosure is within the skill of the person skilled in the art using routine trial and experimentation.

The personal care composition may further comprise one or more additional optional ingredients. Such ingredients include, but are not limited to, polymers, emollients, sunscreens, emulsifiers, preservatives, opacifiers, rheology modifiers, colorants, dyes, preservatives, pH adjustors, propellants, reducing agents, fragrances, foaming agents, tanning agents, depilatory agents, flavors, astringents, antiseptics, deodorants, antiperspirants, insect repellants, bleaches, lighteners, anti-oxidants, moisturizers, organic acids, anti-dandruff agents, adhesives, polishes, strengtheners, fillers, barrier materials, biocides, and mixtures thereof. The particular benefit agent and the quantity to be used for the personal care composition of the present disclosure is within the skill of the person skilled in the art using routine trial and experimentation.

In some embodiments, the personal care composition further comprises one or more of water-soluble polymers. Examples of water-soluble polymers include non-ionic poly (ethylene oxide) polymers having a molecular weight between about 400 kDa and about 4,000 kDa, such as the products sold under the names POLYOX™ (commercially available from Dow Chemical Company), or poly(ethylene oxide) polymers having a molecular weight between about 500 Da and about 10 kDa, such as the products sold under the names CARBOWAX™ (commercially available from Dow Chemical Company). In one embodiment, the personal care composition further comprises a poly(ethylene oxide) polymer having a molecular weight between about 500 kDa and about 2,000 kDa.

In some embodiments, the personal care composition further comprises an optional rheology modifier as a thickener or suspending agent. Examples of thickeners include polymers, for example, modified or unmodified carboxyvinyl polymers, such as the products sold under the names CARBOPOL and PEMULEN (INCI name: Acrylates/C10-30 alkyl acrylate crosspolymer; available from Noveon), polyacrylates and polymethacrylates, such as the products sold under the names LUBRAJEL and NORGEL (commercially available from Guardian), ACULYN (commercially available from Dow Chemical Company), or HISPAGEL (commercially available from Hispano Chimica), polyacrylamides, 2-acrylamido-2-methylpropanesulfonic acid polymers and polymers, which are optionally crosslinked and/or neutralized, for instance the poly(2-acrylamido-2-methyl-propane-sulfonic acid) sold by Clariant (ammonium polyacryldimethyltauramide), emulsified crosslinked anionic polymers of acrylamide and AMPS, such as those sold under the name SEPIGEL 305 (Polyacrylamide/C13-14 Isoparaffin/Laureth-7; from Seppic) and under the name SIMUL-GEL 600 (Acrylamide/Sodium acryloyldimethyltaurate polymer/Isohexadecane/Polysorbate 80; from Seppic), polysaccharide biopolymers, for instance xanthan gum, guar gum, carob gum, acacia gum, scleroglucans, chitin and chitosan derivatives, carrageenans, gellans, alginates, celluloses such as microcrystalline cellulose, cellulose derivatives, associative polymers, for instance associative polyurethanes, polymers comprising at least two hydrocarbon-based lipophilic chains comprising from 6 to 30 carbon atoms, separated with a hydrophilic sequence, such as the polyurethanes sold under the names SERAD FX1010, SERAD FX1100 and SERAD FX1035 (commercially available from Huls America), RHEOLATE 255, RHEOLATE 278 and RHEOLATE 244 (INCI name: Polyether-urea-polyurethane; from Rheox), DW 1206F, DW 1206J, DW 1206B, DW 1206G, and ACRYSOL RM 2020 (commercially available from Dow Chemical Company).

Colorants include pigments, which are used especially in make-up, including metal oxide pigments, titanium dioxide, optionally surface-treated, zirconium oxide or cerium oxide, zinc oxide, iron oxide (black, yellow or red), chromium oxide, manganese violet, ultramarine blue, chromium hydrate and ferric blue, carbon black, pigments of barium, strontium, calcium or aluminum (for example D&C or FD&C), cochineal carmine, micacoated with titanium or with bismuth oxychloride, titanium mica with iron oxides, titanium mica with, especially, ferric blue or chromium oxide, titanium mica with an organic pigment, nacreous pigments based on bismuth oxychloride, goniochromatic pigments, for example pigments with a multilayer interference structure, reflective pigments, for example particles with a silver-coated glass substrate, glass substrate coated with nickel/chromium/molybdenum alloy, glass substrate coated with brown iron oxide, particles comprising a stack of at least two polymer layers, for instance MIRROR GLITTER (commercially available from 3M).

Dyes include water-soluble dyes such as copper sulfate, iron sulfate, water-soluble sulfopolyesters, rhodamines, natural dyes, for instance carotene and beetroot juice, methylene blue, caramel, the disodium salt of tartrazine and the disodium salt of fuschin, and mixtures thereof. Liposoluble dyes from the list above can also optionally be used.

Preservatives include, but are not limited to, alcohols, aldehydes, methylchloroisothiazolinone and methylisothiazolinone, p-hydroxybenzoates, and in particular methylparaben, propylparaben, glutaraldehyde and ethyl alcohol.

The pH adjusters include, but are not limited to, inorganic and organic acids and bases and in particular aqueous ammonia, citric acid, phosphoric acid, acetic acid, and sodium hydroxide.

Reducing agents include ammonium thioglycolate, hydroquinone and sodium thioglycolate.

Fragrances can be aldehydes, ketones, or oils obtained by extraction of natural substances or synthetically produced as described above. Often, fragrances are accompanied by auxiliary materials, such as fixatives, extenders, stabilizers and solvents.

Biocides include antimicrobials, bactericides, fungicides, algaecides, mildicides, disinfectants, antiseptics, and insecticides.

Particularly useful personal care compositions of the disclosure are those that are a shampoo, a rinse-off conditioner, a leave-in conditioner, cleansing conditioner, or a body wash. In one embodiment, the personal care composition of the disclosure is a shampoo, a rinse-off conditioner, or a leave-in conditioner. In another embodiment, the personal care composition of the disclosure is a shampoo or a rinse-off conditioner. In another embodiment, the personal care composition of the disclosure is a 2-in-1 shampoo (shampoo-conditioner composition). In use, the personal care compositions are applied to hair or skin. In one embodiment, applying the present personal care compositions constitute a method of conditioning hair.

The personal care compositions are generally prepared by conventional methods such as those known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The personal care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

Definitions

The following terms and expressions used have the indicated meanings.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the personal care composition). All mol % values are based on the moles of the active compounds. All solution viscosities are measured at about 25.0° C.

The term "cosmetically acceptable" refers to ingredients typically used in personal care compositions.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

EXAMPLES

The methods of the disclosure are illustrated further by the following examples, which are not to be construed as limiting the disclosure in scope or spirit to the specific procedures and in them.

Example 1

Synthesis of Morpholine-modified Guar

A 500 mL four-necked round-bottomed flask is fitted with a stirring paddle and motor, a nitrogen inlet, an immersion thermocouple connected to a heating mantle and controller, a rubber serum cap, a pressure-equalizing addition funnel and a cold water condenser with a mineral oil bubbler. The resin kettle is charged with 39.36 g (35.1 g contained, 139.3 millimoles) of guar gum (Dabur DAVISCO DHV-74) and a mixture of 210 g of technical grade acetone and 23 g of distilled water. The addition funnel is charged with a solution of 32.75 g of 4-(2-chloroethyl)morpholine hydrochloride in 46.0 g of water. The mixture is purged with nitrogen for one hour while stirring. A steady bubbling rate of about one bubble a second is a sufficient nitrogen purge rate.

After purging the slurry for one hour, the aqueous solution of 4-(2-chloroethyl)morpholine hydrochloride is added to the slurry dropwise over 15 minutes with stirring. The slurry is then stirred for an additional 30 minutes, and using a plastic syringe 18.76 g (234.5 millimoles) of 50% aqueous sodium hydroxide solution are added dropwise over approximately 10 minutes. During the addition, the guar slurry changes from beige to bright yellow. The slurry is gently heated with a heating mantle to 40° C. and held at 40° C. for 2 hours. The slurry is then cooled to room temperature and neutralized by adding 13 g of glacial acetic acid by syringe and stirring for 15 minutes. The polymer is recovered by vacuum filtration and washed in a Waring blender five times with a mixture of 380 mL of acetone and 90 mL of distilled water and twice with 400 mL of pure acetone.

The polymer is then dried in vacuo at 50° C. overnight, yielding 44.41 g of an off-white powder. The polymer (Ex-1) contained 3.16% volatiles (mass loss on drying at 110° C. for one hour), 5.96% ash (as sodium acetate, determined by wet ashing as described in ASTM D-2364), and a Kjeldahl nitrogen content (corrected for ash and volatiles) of 2.14%. The 1% aqueous solution (corrected for ash and volatiles) of morpholine-modified guar polymer (Ex-1) was measured using a TA Instruments AR-2000 oscillatory rheometer fitted with a cone and plate geometry, and the viscosity at a shear rate of 6.31 sec$^{-1}$ was found to be 3053 mPa-sec and at a shear rate of 10 sec$^{-1}$ was found to be 2274 mPa-sec. The 1% Brookfield viscosity at 25.0° C. and 30 rpm (spindle #4) was found to be 3833 mPa-sec.

Example 2

Synthesis of Morpholine-modified Hydroxypropyl Guar

A 500 ml resin kettle is fitted with a mechanical stirring paddle, a nitrogen inlet, a serum cap, a subsurface thermocouple connected to a heating mantle and controller, and a reflux condenser connected to a mineral oil bubbler. The resin kettle is charged with 39.73 g (33.35 g contained, 119.0 millimoles) Dabur HPG-8 hydroxypropyl guar, 12.05 g (64.8 millimoles) of 4-(2-chloroethyl)morpholine hydrochloride, and a mixture of 180 g of isopropyl alcohol and 60 g of water. While stirring the mixture, the reactor is purged with nitrogen for one hour to remove any entrained oxygen.

While stirring under nitrogen, a solution of 14.74 g (184.3 millimoles) of 50% aqueous sodium hydroxide solution is added dropwise under nitrogen over one minute using a syringe. The slurry is allowed to stir for fifteen minutes, then the mixture is heated to 60° C. and held at that temperature with stirring under nitrogen for 3 hours.

The slurry is cooled to room temperature and neutralized by adding 11.0 g of glacial acetic acid and stirring for 15 minutes. The polymer is collected by vacuum filtration and washed in a Waring blender: five times with a mixture of 350 ml of acetone and 100 ml of water, and twice with 400 ml of pure acetone. The polymer is dried overnight in vacuo at 50° C., yielding 36.2 g of polymer (Ex-2) with a volatiles content of 6.14%, an ash content of 6.52% (as sodium acetate), and a Kjeldahl nitrogen content of 1.76% (corrected for ash and volatiles). The 1% aqueous solution (corrected for ash and volatiles) of morpholine-modified hydroxypropyl guar polymer (Ex-2) was measured using a TA Instruments AR-2000 oscillatory rheometer fitted with a cone and plate geometry, and the viscosity at a shear rate of 6.31 sec$^{-1}$ was found to be 1103 mPa-sec.

Example 3

Synthesis of Imidazole-modified Guar

The glycidyl imidazole alkylating agent (1-glycidyl imidazole) is prepared by the following procedure. A 125 ml Erlenmeyer flask is charged with 7.25 g of imidazole (106.5 mmoles), 8.51 g of 50% aqueous sodium hydroxide solution (106.4 mmoles), and 28.00 g of distilled water. The solution is gently heated to 50° C. while stirring on a magnetic hot plate. While holding at 50° C., 9.81 g of epichlorohydrin (106.0 mmoles) are added by pipet in small portions with stirring. The epichlorohydrin is insoluble in the aqueous mixture, but as it reacts, the solution becomes homogeneous. The epichlorohydrin addition rate is controlled to keep the temperature of the aqueous solution between 50° C. and 55° C., removing the flask from the hot plate and cooling in water as required. The addition time for the epichlorohydrin is about 30 minutes. After the epichlorohydrin addition was complete and the solution was homogeneous, the mixture was stirred for 30 minutes at 60° C. The light straw-colored solution is then ready for use, but can be stored overnight in the refrigerator.

A 500 ml resin kettle is fitted with a mechanical stirring paddle, a nitrogen inlet, a serum cap, a subsurface thermocouple connected to a heating mantle and controller, a serum cap, and a reflux condenser connected to a mineral oil bubbler. The resin kettle is charged with 30.00 g (contained) Weatherford WGA-15 guar gum (119.0 mmoles), 170 g of acetone, and 6 g of distilled water. While stirring the mixture, the reactor is purged with nitrogen for one hour to remove any entrained oxygen.

While stirring under nitrogen, 4.33 g of 50% aqueous sodium hydroxide solution (54.1 mmoles) are added dropwise over five minutes using a syringe. The slurry changed from beige to greenish yellow and the mixture is then allowed to stir for 30 minutes under nitrogen. Then, the solution of 1-glycidyl imidazole as prepared above is added dropwise by syringe over 10 minutes under nitrogen. Heat is then applied to the slurry, which is allowed to reflux under nitrogen for 2 hours.

The slurry is cooled to room temperature and neutralized by adding 8.00 g of glacial acetic acid and stirring for 15 minutes. The polymer is collected by vacuum filtration and washed in a Waring blender: five times with a mixture of 400 ml of acetone and 100 ml of water, and twice with 500 ml of pure acetone. The polymer (Ex-3) is dried overnight in vacuo at 50° C., yielding 36.44 g of polymer (Ex-3) with a volatiles content of 5.86%, an ash content of 4.22% (as sodium acetate), and a Kjeldahl nitrogen content of 2.65% (corrected for ash and volatiles). The 1% Brookfield viscosity at 25.0° C. and 30 rpm (spindle #3) was found to be 2891 mPa-sec.

Example 4

Synthesis of Diethylaminoethyl-modified Guar

A 1000 ml four-necked round-bottomed flask is fitted with a stirring paddle and motor, a nitrogen inlet, an immersion thermocouple connected to a heating mantle and controller, a pressure-equalizing addition funnel, a rubber serum cap, and a cold water condenser with a mineral oil bubbler. The resin kettle is charged with 78.51 g (70.00 g contained, 0.278 moles) of Dabur DAVISCO DHV-74 guar gum and a mixture of 420 g of technical grade acetone and 47 g of distilled water. An addition funnel is charged with a solution of 25.0 g (0.145 moles) of 2-chloro-N,N-diethylethylamine hydrochloride (N,N-diethylaminoethyl chloride hydrochloride) in 52 g of distilled water. The mixture is purged with nitrogen for one hour while stirring. A steady bubbling rate of about one bubble a second is a sufficient nitrogen purge rate.

After purging the slurry for one hour, the aqueous solution of 2-chloro-N,N-diethylethylamine hydrochloride is added to the slurry dropwise over 15 minutes with stirring. The slurry is then stirred for an additional 30 minutes, and 21.2 g of 50% aqueous sodium hydroxide solution (0.265 moles) are added dropwise over approximately 10 minutes. During the addition, the guar slurry changes from beige to bright yellow. The slurry is stirred for an additional 10 minutes, then heat is applied and the mixture is held at 40° C. for 2 hours.

The slurry is then cooled to room temperature and neutralized by adding 19 g of glacial acetic acid by syringe and stirring for 15 minutes. The polymer is recovered by vacuum filtration and washed in a Waring blender five times with a mixture of 600 ml of acetone and 175 ml of distilled water and twice with 800 ml of pure acetone. The polymer is then dried in vacuo at 50° C. overnight, yielding 82.0 g of an off-white powder. The polymer (Ex-4) contained 5.84% volatiles, 1.26% ash (as sodium acetate), and a Kjeldahl nitrogen content (corrected for ash and volatiles) of 2.06%. The 1% aqueous solution (corrected for ash and volatiles) of diethylaminoethyl-modified guar polymer (Ex-4) was measured using a TA Instruments AR-2000 oscillatory rheometer fitted with a cone and plate geometry, and the viscosity at a shear rate of 6.31 sec$^{-1}$ was found to be 3099 mPa-sec and at a shear rate of 10 sec$^{-1}$ was found to be 2381 mPa-sec.

Example 5

Synthesis of Morpholine-modified Guar

A 1000 ml four-necked round-bottomed flask is fitted with a stirring paddle and motor, a nitrogen inlet, an immersion thermocouple connected to a heating mantle and controller, a pressure-equalizing addition funnel, a rubber serum cap, and a cold water condenser with a mineral oil bubbler. The resin kettle is charged with 78.51 g (70.00 g contained, 0.278 moles) of Dabur DAVISCO DHV-74 guar gum and a mixture of 420 g of technical grade acetone and 47 g of distilled water. An addition funnel is charged with a solution of 60.0 g (0.322 moles) of 4-(2-chloroethyl)morpholine hydrochloride in 90 g of distilled water. The mixture is purged with nitrogen for one hour while stirring. A steady bubbling rate of about one bubble a second is a sufficient nitrogen purge rate.

After purging the slurry for one hour, the aqueous solution of 4-(2-chloroethyl)morpholine hydrochloride is added to the slurry dropwise over 15 minutes with stirring. The slurry is then stirred for an additional 30 minutes, and 35.0 g of 50% aqueous sodium hydroxide solution (0.438 moles) are added dropwise over approximately 10 minutes. During the addition, the guar slurry changes from beige to bright yellow. The slurry is stirred for an additional 10 minutes, then heat is applied and the mixture is held at 40° C. for 2 hours.

The slurry is then cooled to room temperature and neutralized by adding 19 g of glacial acetic acid by syringe and stirring for 15 minutes. The polymer is recovered by vacuum filtration and washed in a Waring blender five times with a mixture of 600 ml of acetone and 175 ml of distilled water and twice with 800 ml of pure acetone. The polymer is then dried in vacuo at 50° C. overnight, yielding 86.7 g of an off-white powder. The polymer (Ex-5) contained 6.41% volatiles, 2.83% ash (as sodium acetate), and a Kjeldahl nitrogen content (corrected for ash and volatiles) of 1.89%. The 1% aqueous solution (corrected for ash and volatiles) of morpholine-modified guar polymer (Ex-5) was measured using a TA Instruments AR-2000 oscillatory rheometer fitted with a cone and plate geometry, and the viscosity at a shear rate of 6.31 sec$^{-1}$ was found to be 2702 mPa-sec.

Example 6

Shampoo Formulation

The polymer of interest is first made into a 1% solution in the following manner: 1.5 g of polymer powder is added to beaker containing 148.38 g water, mixed for 2 hours while cooling and maintaining the beaker in an ice bath. The water bath is heated to 50-55° C. and mixed for an additional 2 hours. The bath is cooled to 25° C. and preservative is added, and mixed for an additional 10 minutes. Water is added to adjust for water loss and the solution is mixed for an additional 10-15 minutes.

The silicone containing shampoo formulation is made in the following manner in accordance with the amounts listed in Table 1: In an empty beaker, the surfactants and water are added and mixed until uniform, then heated to 80° C. Ethylene glycol distearate is added and mixed for 15 minutes while maintaining the temperature. This mixture is cooled to 25° C. and the speed is increased to 750 rpm. Silicone polymer is added and mixed for 30 minutes. The polymer solution is slowly added and mixed for 30 minutes. Citric acid and preservative are added and the solution is mixed for an additional 10 minutes. Additional water is added to make up for any water loss and the solution is mixed for another 10-15 minutes.

The non-silicone containing shampoo formulation is made in the following manner in accordance with the amounts listed in Table 1: In an empty beaker, surfactants and water are added and mixed until uniform, then heated to 65° C. and mixed at 650 rpm for 30 minutes while maintaining the temperature. Polymer solution is slowly added and the solution is mixed for 30 minutes. This mixture is cooled to 25° C. Citric acid and preservative are added and the solution is mixed for 10 minutes. Additional water is then added to make up for any water loss and the solution is mixed for another 10-15 minutes.

TABLE 1

| Formulation | % active as received | % active - Final | Shampoo with Silicone | Shampoo without Silicone |
|---|---|---|---|---|
| Water | NA | NA | 1.71 | 0.10 |
| Sodium Laureth Sulfate | 25% | 15.2 | 91.20 | 91.17 |
| Cocoamphocarboxyglycinate | 38.5% | 2.66 | 10.38 | 10.40 |
| Ethylene Glycol Distearate | 100.0% | 2 | 3.02 | — |
| Dow Corning 1664 | 50.0% | 1 | 3.08 | — |

TABLE 1-continued

| Formulation | % active as received | % active - Final | Shampoo with Silicone | Shampoo without Silicone |
|---|---|---|---|---|
| Conditioning Polymer[a] | 1.0-1.5% | 0.25-0.30 | 37.63 | 45.09 |
| Citric Acid | 10% | 0.22 | 3.32 | 3.30 |
| Preservative | 1.5% | 0.0012 | 0.12 | 0.12 |
| Total Batch Weight | | | 150.46 | 150.18 |
| Water loss adjustment | | | 1.29 | 3.11 |

[a]Depending on the desired end formulation, the "Conditioning Polymer" is the guar derivative of the disclosure (e.g., 4-morpholinylethyl guar), or diethylaminoethyl guar, or JAGUAR™ C-13S, or simply water in the case of the control formulation.

When formulated as described above, this personal care composition had a pH around 5.8, a viscosity (RV5/20 rpm) of 19,720 and a pearly white appearance.

Wet Comb Test Method

Swatches of European brown hair (as available from International Hair Importers) are prepared by the following prewash procedure: hair tresses are hydrated for 30 seconds flipping over the hair every 15 seconds (tap water at 38° C. and at a flow rate of 0.40 gallon/minute). The excess water is squeezed out using the middle and index fingers while maintaining a firm and even pressure with a downward motion. 10% Tergitol 15-S-9 is then applied (10% by hair tress weight; i.e., 0.3 g of shampoo to 3.0 g hair tress). Tergitol is worked into the hair stroking the hair with the thumb, index finger and middle finger using the top to bottom motion for 30 seconds, flipping over every 15 seconds. The hair is then rinsed for 30 seconds, flipping the hair tress after every 15 seconds. Finally, the hair is combed and let air dry.

The pre-washed hair tress are hydrated for 30 seconds (tap water at 38° C. and at a flow rate of 0.40 gallon/minute), flipping the hair tress every 15 seconds. Shampoo formulation (10% by hair tress weight) is applied to the pre-washed hair tress. The shampoo is worked thoroughly into the hair stroking the hair with the thumb, index and middle fingers using a top to bottom motion for 30 seconds, flipping the hair every 15 seconds. Treated hair is rinsed with 38° C. tap water at a flow rate of 0.4 gal/min for 30 seconds, flipping the hair every 15 seconds. The hair tress is additionally manipulated at this point to assure no residual treatment remains on the hair tress.

A wide tooth comb is used to comb through hair tress twice, once from the front and once from the back. The fine tooth side of the comb is used to comb through hair twice, again once from the front and once from the back. The hair tress is squeezed using middle and index fingers lightly while maintaining even pressure with a downward motion to align the hair tress.

The hair is then placed in a fine tooth comb on a Dia-Stron MTT-170. The hair tress is pulled upward and hair tress is clamped to the Dia-Stron holder. The Dia-Stron then combs through the hair and stops just below the hair tress. After the hair tress is combed through by the Dia-Stron, the hair tress is re-aligned by squeezing the hair tress using middle and index fingers lightly while maintaining even pressure with a downward motion to align the hair tress and hold it in place. The hair is gently lifted out of the way so it is not tangled as the comb returns to base position. The hair is then gently pushed into the comb on the Dia-Stron. The hair is wiggled back and forth to release any tension on the comb. The process is repeated to collect a total of 11 readings/traces.

Results: As shown in FIG. 1, a shampoo containing 4-morpholinylethyl guar provides excellent performance similar or better than shampoos containing its quaternary counterparts (cationic guar, JAGUAR™ C-13S) and diethylaminoethyl guar in both conditioning and assisted deposition of beneficial agents. This is shown by the low combing force, indicating a reduction in friction of the hair exhibited after application of a shampoo containing 4-morpholinylethyl guar.

Example 7

Shampoo Formulation

Shampoos are formulated consistent with the manner described in Example 6 above.

Panel Testing of Shampoo Formulations 5.0 g tresses of European Brown Virgin hair (as available from International Hair Importers) are prewashed for 1 minute with approximately 0.5 g of Tergitol 15-S-9 and well rinsed (1 minute or longer). For evaluation, tresses are pre-wetted and then washed with 1.0 g of formulated shampoo for 1 minute, flipping the tress over after approximately 30 seconds. Strokes are in a circular motion from root to tip end. The treated tress is then rinsed with 38° C. tap water flowing at 0.4 gallons/minute for 1 minute, flipping the tress over at approximately 30 seconds. Some manipulation of the tress is done to ensure no residual treatment remains on the hair tress. Hair tresses are minimally combed to align hair fibers prior to panelist evaluations.

Five panelists are asked to feel and comb wet hair tresses, in duplicate. Each panelist was asked to compare (A vs. B) and state which tress was smoother to comb/feel—"same" was disallowed. The score out of 100 is reported for each comparison.

Figure 4:
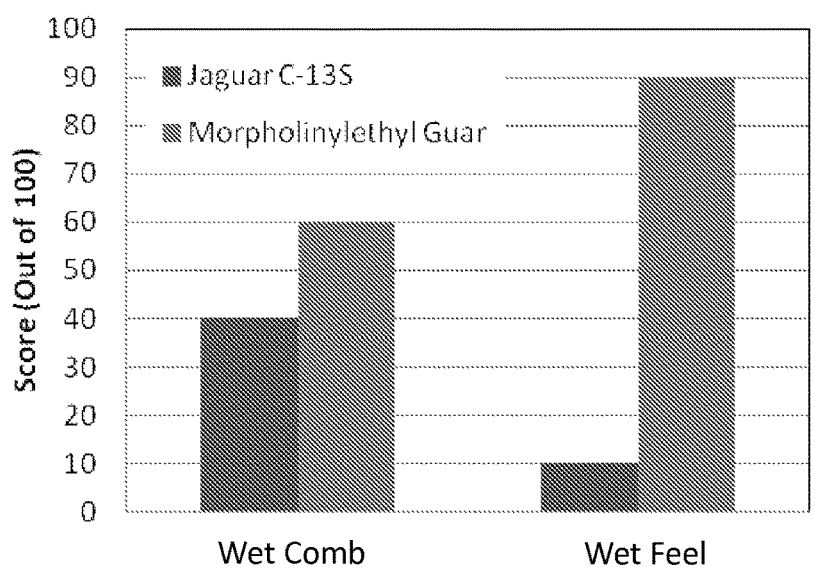
FIG. 4 is a graph depicting the panel test results of a shampoo containing 4-morpholinylethyl guar and a shampoo containing a cationic guar (JAGUAR™ C-13S).

Results: As shown in FIG. 4, a shampoo containing 4-morpholinylethyl guar can provide superior performance characteristics to shampoos containing JAGUAR™ C-13S. The graph clearly shows a preference for the wet sensorial feel of hair washed with a shampoo containing 4-morpholinylethyl guar over hair washed with a shampoo containing JAGUAR™ C-13S. In other categories, such as wet combing, the hair tresses are found to have similar performance.

Example 8

Shampoo Formulation

The shampoo formulation is made in the following manner with the amounts listed in Table 2: Add 80% of the total amount of formulation water while stirring to make a dispersion of the polymers (Phase A). Disodium ethylenediaminetetraacetate dihydrate is added followed by Phase B materials. The pH is adjusted to 5.5-6.5 and then the materials in Phase C are added. Diluted sodium chloride is added along with the remainder of water to adjust the viscosity. The viscosity of the shampoo was 5000-7000cP.

TABLE 2

| Phase | Components | Shampoo Formulation (%) |
|---|---|---|
| A | Water | Qsp 100 |
| A | Conditioning Polymer[a] | 0.15 |
| A | Polyox WSR N60K | 0.15 |
| A | Disodium ethylenediaminetetraacetate dihydrate | 0.10 |
| B | Sodium Lauryl Ether Sulfate (27%) | 35.0 |
| B | Cocoamidopropyl Betaine | 7.0 |
| C | Preservative | 0.10 |
| D | Water | 20.0 |
| D | Sodium Chloride | 1.7 |

[a]Depending on the desired end formulation, the "Conditioning Polymer" is a guar derivative of the disclosure (e.g., 4-morpholinylethyl guar), or EcoSmooth™ 100, or UCARE™ JR-30M.

Build Up Test Method

European Virgin Brown hair tresses (as available from International Hair Importers) are prewashed in a manner similar to the prewash description in Example 6. The prewashed hair is then hydrated by placing it directly under flowing water at 38° C. (±1° C.) for 1 minute, flipping over the hair tress after 30 sec. 0.3 g of formulated shampoo is applied to a 3 g hair tress extension or 0.5 g of product is applied to a 5 g hair tress extension. The tress is massaged for 15 seconds on each side, generating foam, and then rinsed with water at 38° C. (±1° C.) for 15 seconds, alternating sides. Using fingers and even pressure down the tress, excess water is removed from the tress. A placebo hair tress is washed in a similar manner that that described above, however 27% sodium lauryl ether sulfate is used instead of the shampoo formulation. The hair tress is allowed to dry at room temperature for 24 hours and then this procedure is repeated for 5 consecutive days. When dry, the tress is evaluated for visual and sensorial performance. The washing is then repeated for another 5 consecutive days. Again, once the tress is dry it is evaluated for visual and sensorial performance. Evaluation in FIG. 2 was done after 10 washes and 24 hours of dry time.

Figure 2:
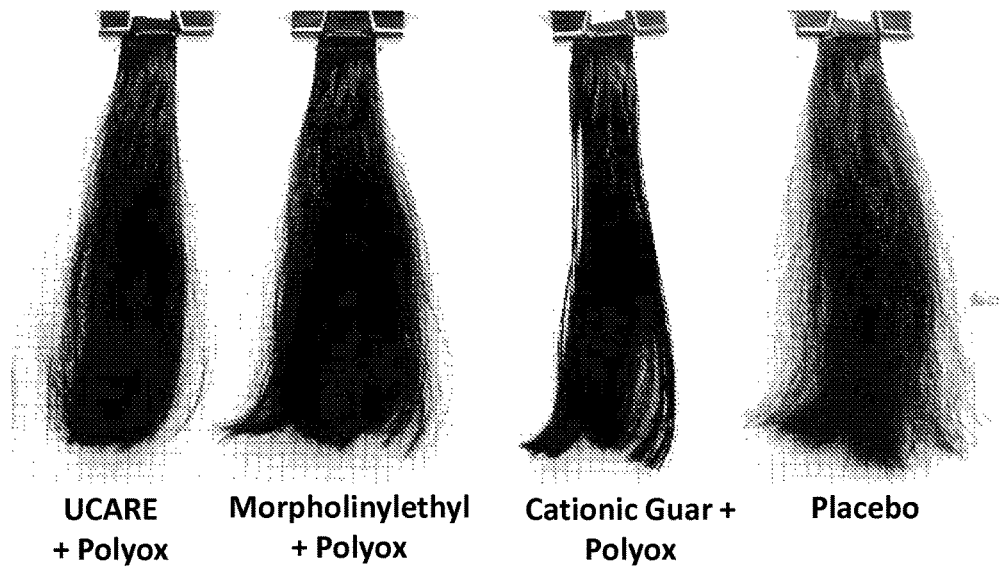
FIG. 2 is an image depicting the results of buildup resistance test of a shampoo containing 4-morpholinylethyl guar, a shampoo containing a cationic guar (EcoSmooth™ 100, available from Dow Chemical Company), and a shampoo containing UCARE™ JR-30M (available from Dow Chemical Company) polymers.

Results: As shown in FIG. 2, a shampoo with 4-morpholinylethyl guar unexpectedly provides improved buildup resistance when compared a shampoo to containing EcoSmooth™ 100, a cationic guar. Buildup performance of shampoo containing 4-morphollinylethyl is comparable or better than a similar composition containing UCARE™ JR-30M polymer (available from Dow Chemical Company), which are known by those skilled in the art to have good resistance to undesirable build up.

Example 9

Shampoo Formulation

The shampoo was formulated in a similar manner to the procedure and amounts described in Example 8.

High Humidity Test Method

Brazilian hair tresses (as available from International Hair Importers) are prewashed and washed one time in a manner similar to that described in Example 8. The hair is then allowed to dry inside a climate chamber and visually evaluated at the initial time point, 6 hours, and 24 hours.

Figure 3:
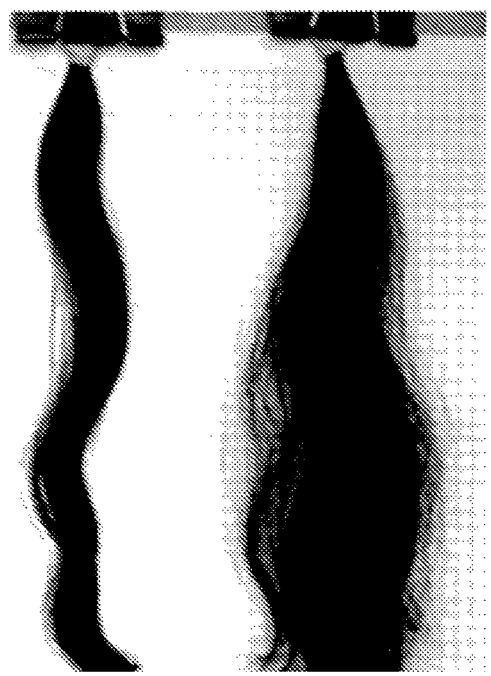
FIG. 3 is an image depicting the results of humidity resistance test of a shampoo containing 4-morpholinylethyl guar and a shampoo containing a cationic guar (EcoSmooth™ 100).

Results: As can be seen in FIG. 3, a shampoo with 4-morpholinylethyl guar unexpectedly provides improved humidity resistance when compared to a shampoo containing Ecosmooth 100, a cationic guar. The photo in FIG. 3 was taken after 24 hours in the climate chamber and shows the lower volume and frizz after use of a shampoo with 4-morpholinylethyl guar compared to use of the shampoo to containing cationic guar.

Example 10

Aquatic Toxicity Test Method

Screening assays were conducted to evaluate the acute aquatic toxicity of 4-morpholinylethyl guar (as prepared in Example 5) and diethylaminoethyl guar (as prepared in Example 4) to the cladoceran *Daphnia magna* (representative freshwater invertebrate) and the *Oncorhynchus mykiss* (representative freshwater fish. Studies were based on the following standard test guidelines:
1) OECD (2004). Organization for Economic Cooperation and Development. OECD Guidelines for Testing Chemicals, No. 202, *Daphnia* sp., Acute Immobilization Test.
2) OECD (1992). Organization for Economic Cooperation and Development. OECD Guidelines for Testing Chemicals, No. 203, Fish Acute Toxicity Test.

Briefly, daphnids were exposed for 48 hours and fish for 96 hours to test solutions containing 0 (control), 10, 100 and 300 mg/L for each test compound prepared in laboratory dilution water. Five daphnids or fish were exposed at each test concentration. Observations of immobility (defined as the inability to move within 15 seconds after being prodded) and abnormal behavior were made for daphnids while observations of mortality and abnormal behavior were made for fish.

Results: When tested for aquatic toxicity, 4-morpholinylethyl guar was non-toxic to both daphnids and fish, with $EC_{50}$ and $LC_{50}$ values of >300 mg/L and a no-observed effect concentration (NOEC) of 300 mg/L, the highest concentration tested. In contrast, diethylaminoethyl guar was more toxic, with an $EC_{50}$=155 mg/L for daphnids and $LC_{50}$<10 mg/L for fish. These results are shown in Table 3.

TABLE 3

| | diethylaminoethyl guar | | 4-morpholinylethyl guar | |
|---|---|---|---|---|
| Endpoint[a] | $E/LC_{50}$ (mg/L) (95% Confidence Intervals) | NOEC (mg/L) | $E/LC_{50}$ (mg/L) (95% Confidence Intervals) | NOEC (mg/L) |
| Daphnia immobility | 155[b] (83-290) | 100 | >300 (NC) | 300 |
| Fish mortality | <10[c] (NC) | NA | >300 (NC) | 300 |

[a]All calculations based on nominal concentrations.
[b]The mortality proportions were not monotonically increasing, so adjustments were made prior to Spearman-Karber estimation.
[c]Because all fish died, an $LC_{50}$ could not be calculated.
NC = Not able to be calculated
NA = Not applicable It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:
1. A personal care composition, comprising:
one or more anionic or amphoteric surfactants, and
a guar derivative which is 4-morpholinylethyl guar.

2. A personal care composition according to claim 1, wherein guar derivative has a viscosity of about 500 to about 10,000 mPa-sec in a 1% aqueous solution corrected for ash and volatiles.

3. A personal care composition according to claim 1, wherein the guar derivative has molecular weight range from about 50 to about 5,000 kDa.

4. A personal care composition according to claim 1, wherein the guar derivative has a Kjeldahl nitrogen content from about 0.02% to about 7.5%.

5. A personal care composition of claim 4, wherein the guar derivative has a Kjeldahl nitrogen content of from about 1% to about 2.5%.

6. A personal care composition according to claim 1, wherein the guar derivative is present at from about 0.05 weight % to about 2 weight % of the composition.

7. A personal care composition according to claim 1, where composition further comprises a nonionic surfactant.

8. A personal care composition according to claim 1, wherein the surfactant is an anionic surfactant.

9. A personal care composition of claim 8, wherein the surfactant is at from about 1 weight % to about 25 weight % of the composition.

10. A personal care composition of claim 7, wherein the surfactant is present at from about 1 weight % to about 25 weight % of the composition.

11. A personal care composition according to claim 1 further comprising a silicone.

12. A personal care composition of claim 11, wherein the silicone is present at from about 0.01 weight % to about 5 weight % of the composition.

13. A personal care composition according to claim 11, wherein the guar derivative has molecular weight range from about 50 to about 5,000 kDa.

14. A personal care composition of claim 13, wherein the guar derivative has a Kjeldahl nitrogen content of from about 1% to about 2.5%.

15. A personal care composition according to claim 14, wherein the guar derivative is present at from about 0.05 weight % to about 2 weight % of the composition.

16. A personal care composition according to claim 1, which is a shampoo, a rinse-off conditioner, a leave-in conditioner, a cleansing conditioner, or a body wash.

17. A personal care composition, comprising:
a surfactant system comprising a non-ionic surfactant and an amphoteric surfactant,
a non-ionic poly(ethylene oxide) polymer having a molecular weight between about 400 kDa and about 4,000 kDa; and
a guar derivative which is 4-morpholinylethyl guar.

18. A personal care composition, comprising:
a surfactant system comprising a non-ionic surfactant and an amphoteric surfactant, and
a guar derivative which is 4-morpholinylethyl guar.

* * * * *